(12) United States Patent
Sodickson et al.

(10) Patent No.: US 10,092,253 B2
(45) Date of Patent: Oct. 9, 2018

(54) SYSTEM, METHOD, AND COMPUTER ACCESSIBLE MEDIUM FOR MODULATING X-RAY BEAM INTENSITY

(71) Applicant: New York University, New York, NY (US)

(72) Inventors: Daniel K. Sodickson, Larchmont, NY (US); Aaron Sodickson, Wayland, MA (US); Ricardo Otazo, New York, NY (US)

(73) Assignees: NEW YORK UNIVERSITY, New York, NY (US); BRIGHAM AND WOMEN'S HOSPITAL, Boston, MA (US)

( * ) Notice: Subject to any disclaimer, the term of this patent is extended or adjusted under 35 U.S.C. 154(b) by 113 days.

(21) Appl. No.: 14/861,312

(22) Filed: Sep. 22, 2015

(65) Prior Publication Data
US 2016/0007938 A1    Jan. 14, 2016

Related U.S. Application Data

(63) Continuation-in-part of application No. PCT/US2014/031609, filed on Mar. 24, 2014.
(Continued)

(51) Int. Cl.
*A61B 6/03* (2006.01)
*A61B 6/06* (2006.01)
(Continued)

(52) U.S. Cl.
CPC .............. *A61B 6/032* (2013.01); *A61B 6/06* (2013.01); *A61B 6/405* (2013.01); *A61B 6/4035* (2013.01);
(Continued)

(58) Field of Classification Search
CPC .......... A61B 6/032; A61B 6/06; A61B 6/405; A61B 6/4085; A61B 6/482; A61B 6/54; A61B 6/542; A61B 6/583; G01N 23/046
(Continued)

(56) References Cited

U.S. PATENT DOCUMENTS 4,241,404 A * 12/1980 Lux .................. A61B 6/032
                                                     378/160
4,506,374 A *  3/1985 Flynn ................ G01T 1/2985
                                                     250/363.06
(Continued)

OTHER PUBLICATIONS

Jakob Sauer Jøgensen, Sparse Image Reconstruction in Computed Tomography, Ph.D. Dissertation, Technical University of Demark, 2013.*
(Continued)

*Primary Examiner* — Allen C. Ho
(74) *Attorney, Agent, or Firm* — Hunton Andrews Kurth LLP

(57) ABSTRACT

An imaging system for imaging a portion(s) of an anatomical structure can be provided. For example, an x-ray source first arrangement can provide x-ray radiation, and a multi-hole collimator second arrangement can be provided in a path of the x-ray radiation, and can be configured to undersample the radiation beam which can be forwarded to the portion(s) of the anatomical structure. A third hardware arrangement can be configured to receive a further x-ray radiation from the portion(s) that can be based on the undersampled x-ray radiation.

19 Claims, 14 Drawing Sheets

Related U.S. Application Data

(60) Provisional application No. 61/804,415, filed on Mar. 22, 2013.

(51) Int. Cl.
*A61B 6/00* (2006.01)
*G01N 23/046* (2018.01)

(52) U.S. Cl.
CPC ............ *A61B 6/482* (2013.01); *A61B 6/5205* (2013.01); *A61B 6/54* (2013.01); *A61B 6/542* (2013.01); *A61B 6/4085* (2013.01); *A61B 6/583* (2013.01); *G01N 23/046* (2013.01)

(58) Field of Classification Search
USPC ............ 378/2, 16, 62, 98.9, 98.11, 146–153
See application file for complete search history.

(56) References Cited

U.S. PATENT DOCUMENTS

| | | | | |
|---|---|---|---|---|
| 4,677,681 A * | 6/1987 | Klausz | ............... | A61B 6/025 250/363.07 |
| 4,819,259 A | 4/1989 | Tanaka | | |
| 5,812,629 A | 9/1998 | Clauser | | |
| 6,396,902 B2 * | 5/2002 | Tybinkowski | ......... | G21K 1/025 378/148 |
| 6,480,565 B1 * | 11/2002 | Ning | ............... | A61B 6/032 378/20 |
| 6,850,594 B2 * | 2/2005 | Sembritzki | ............ | A61B 6/542 378/108 |
| 6,876,718 B2 * | 4/2005 | Tang | ............... | A61B 6/032 378/4 |
| 6,987,831 B2 * | 1/2006 | Ning | ............... | A61B 6/032 378/20 |
| 7,072,436 B2 * | 7/2006 | Pelc | ............... | A61B 6/032 378/12 |
| 7,145,981 B2 * | 12/2006 | Pelc | ............... | A61B 6/032 378/9 |
| 7,310,410 B2 * | 12/2007 | Sohal | ............... | G21K 1/04 378/150 |
| 7,382,853 B2 * | 6/2008 | Arenson | ............ | A61B 6/4241 378/19 |
| 7,463,712 B2 * | 12/2008 | Zhu | ............... | A61B 6/5282 378/2 |
| 7,623,614 B2 * | 11/2009 | Shefsky | ............ | G01N 23/02 378/2 |
| 8,090,089 B2 * | 1/2012 | Tischenko | ............ | G06T 11/005 378/147 |
| 8,111,893 B2 * | 2/2012 | Chen | ............... | G06T 11/006 324/307 |
| 8,189,735 B2 * | 5/2012 | Khare | ............... | G06T 11/006 378/4 |
| 8,194,937 B2 * | 6/2012 | Chen | ............... | G06T 11/006 382/118 |
| 8,204,172 B1 * | 6/2012 | Hsieh | ............... | G06T 11/006 378/4 |
| 8,218,907 B2 * | 7/2012 | Chen | ............... | G06T 11/006 382/294 |
| 8,310,233 B2 * | 11/2012 | Trzasko | ............ | G01R 33/561 324/307 |
| 8,326,054 B2 * | 12/2012 | Chen | ............... | A61B 6/032 378/4 |
| 8,374,413 B2 * | 2/2013 | Chen | ............... | G06T 11/006 378/901 |
| 8,483,463 B2 * | 7/2013 | Chen | ............... | G06T 11/006 382/131 |
| 8,587,307 B2 * | 11/2013 | Ying | ............... | G01R 33/5611 324/307 |
| 8,781,243 B2 * | 7/2014 | Chen | ............... | G06T 11/005 382/131 |
| 8,811,700 B2 * | 8/2014 | Wang | ............... | G06T 11/006 382/128 |
| 8,852,103 B2 * | 10/2014 | Rothberg | ............ | A61B 8/4254 600/438 |
| 8,971,481 B2 * | 3/2015 | Tischenko | ............ | A61B 6/032 378/16 |
| 8,989,348 B2 * | 3/2015 | Cox | ............... | G01N 23/04 378/146 |
| 9,013,691 B2 * | 4/2015 | Golub | ............... | H04N 9/045 356/326 |
| 9,036,885 B2 * | 5/2015 | Elad | ............... | G06T 11/006 378/21 |
| 9,070,218 B2 * | 6/2015 | Bernal | ............... | G06T 11/006 |
| 9,121,809 B2 * | 9/2015 | Cox | ............... | G01N 23/04 |
| 9,208,585 B2 * | 12/2015 | Leng | ............... | A61B 6/032 |
| 9,237,874 B2 * | 1/2016 | DeMan | ............... | A61B 6/032 |
| 9,240,071 B2 * | 1/2016 | Mueller | ............... | G06T 15/08 |
| 9,268,046 B2 * | 2/2016 | Carmi | ............... | G01N 23/046 |
| 9,373,159 B2 * | 6/2016 | Amroabadi | ......... | A61B 6/5205 |
| 9,384,566 B2 * | 7/2016 | Chen | ............... | G06T 11/006 |
| 9,418,453 B2 * | 8/2016 | Aspelmeier | ........... | G06T 11/006 |
| 9,460,823 B2 * | 10/2016 | Song | ............... | H05K 7/2039 |
| 9,468,409 B2 * | 10/2016 | Claus | ............... | A61B 6/025 |
| 9,472,000 B2 * | 10/2016 | Dempsey | ............ | G01R 33/4826 |
| 9,508,157 B2 * | 11/2016 | Schafer | ............... | G06T 11/005 |
| 9,691,168 B2 * | 6/2017 | Song | ............... | G06T 11/006 |
| 2004/0264629 A1 | 12/2004 | Tang | | |
| 2006/0023842 A1 | 2/2006 | Sohal et al. | | |
| 2011/0006768 A1 | 1/2011 | Ying et al. | | |
| 2012/0265050 A1 * | 10/2012 | Wang | ............... | A61B 5/055 600/411 |
| 2013/0016805 A1 | 1/2013 | Silver | | |

OTHER PUBLICATIONS

Hugo De Las Heras Gala: "Development and test of a new scanning geometry for Computed Tomography", Jan. 23, 2009, pp. 1-134.

Lei Zhu et al: "X-ray scatter correction for cone-beam CT using moving blocker array", Optical Sensing II, vol. 5745, Apr. 20, 2005, pp. 251-253.

Supplemental European Search Report for European Patent Application No. 14771044.6 dated Aug. 19, 2016.

International Search Report for International Application No. PCT/US2014/031609 dated Aug. 19, 2014.

Written Opinion for International Application No. PCT/US2014/031609 dated Aug. 19, 2014.

Brenner DJ, Hall EJ. "Computed tomography—an increasing source of radiation exposure". N Engl J Med. 2007;357(22):2277-84.

Sodickson A, et al. "Recurrent CT, cumulative radiation exposure, and associated radiation-induced cancer risks from CT of adults". Radiology. 2009; 251(1):175-84.

Berrington de González A, et al. "Projected cancer risks from computed tomographic scans performed in the United States in 2007" Arch Intern Med. 2009;169(22):2071-7.

Mettler FAJ,et al "Radiologic & nuclear medicine studies in the US & worldwide: frequency, radiation dose . . . other radiation sources— 1950-2007" Radiology. 2009;253(2):520-31.

Fazel R, et al. "Exposure to low-dose ionizing radiation from medical imaging procedures" N Engl J Med. 2009;361(9):849-57.

Amis ESJr, et al "American College of Radiology white paper on radiation dose in medicine" J Am Coll Radiol. 2007;4(5):272-84.

Sodickson A. "Strategies for reducing radiation exposure in multi-detector row CT." Radial Clin North Am. 2012;50(1):1-14.

McCollough et al., "CT dose reduction and dose management tools: Overview of available options". Radiographics. 2006;26(2):503-12.

Deak PD, et al. Effects of adaptive section collimation on patient radiation dose in multisection spiral CT. Radiology. 2009; 252(1):140-7.

Shepp LA, Vardi Y. "Maximum likelihood reconstruction for emission tomography". IEEE Trans Med Imag. 1982; 1(2): 113-22.

Grant K, Flohr T. Iterative Reconstruction in Image Space (IRIS). Siemens Healthcare White Paper; A9115-101492. 2010.

Hara AK, et al "Iterative reconstruction technique for reducing body radiation dose at CT: feasibility study". AJR Am J Roentgenol. 2009;193(3):764-71.

(56) References Cited

OTHER PUBLICATIONS

Sodickson A, Weiss M. "Effects of patient size on radiation dose reduction and image quality in low-kVp CT pulmonary . . . dose." Emerg Radiol. 2012;19(5):437-45.
McCollough CH, et al. "Achieving routine submillisievert CT scanning: report from the summit on management of radiation dose in CT" Radiology. 2012;264(2):567-80.
Candès E, et al. "Robust uncertainty principles: Exact signal reconstruction from highly incomplete frequency information". IEEE Trans Inf Theory. 2006;52:489-509.
Donoho D. "Compressed sensing". IEEE Trans Inf Theory. 2006;52:1289-306.
Chen GH, et al "Prior image constrained compressed sensing (PICCS): a method to accurately . . . undersampled projection data sets." Med Phys. 2008;35(2):660-3.
Brown K, et al. "Sparse sampling for CT dose reduction2013: The 12th Int'l Mtg on Fully 3-Dimensional Image Reconstruction in Radiology and Nuclear Medicine". p. 428-31.
Otazo R, et al. "Combination of compressed sensing and parallel imaging for highly accelerated first-pass cardiac perfusion MRI". Magn Reson Med. 2010;64(3):767-76.
Feng L, et al. "Accelerated cardiac T2 mapping using breath-hold multiecho fast spin-echo pulse sequence with k-t FOCUSS". Magn Reson Med. 2011;65(6):1661-9.
Kim D, et al. "Accelerated phase-contrast cine MRI using k-t SPARSE-SENSE". Magn Reson Med. 2012;67(4):1054-64.
Feng L, et al. "Highly accelerated real-time cardiac cine MRI using k-t SPARSE-SENSE." Magn Reson Med. 2012;70(1):64-74.
Knoll F, et al. "Parallel imaging with nonlinear reconstruction using variational penalties". Magn Reson Med. 2012;67(1):34-41.
Chandarana H, et al. "Free-breathing contrast-enhanced multiphase MRI of the liver using a combination of compressed sensing . . . radial sampling" Invest Radiol. 2013;48(1):10-6.
Feldkamp LA, Davis LC, Kress JW. Practical cone-beam algorithm. J Opt Soc Amer. 1984;A1(6):612-9.
Loftus EV, et al. "The epidemiology and natural history of Crohn's disease in population-based patient cohorts . . . review". Ailment Pharmacol Ther. 2002;16(1):51-60.

Wu YW, et al. "Crohn's disease: CT enterography manifestations before and after treatment." Eur J Radiol. 2012;81(1):52-9.
Paulsen SR, et al. "CT enterography: noninvasive evaluation of Crohn's disease and obscure gastrointestinal bleed." Radiol Clin North Am. 2007;45(2):303-15.
Hara AK, Swartz PG. "CT enterography of Crohn's disease." Abdom Imaging. 2009;34(3):289-95.
Huprich JE, Fletcher JG. "CT enterography: principles, technique and utility in Crohn's disease." Eur J Radiol. 2009;69(3):393-7.
Herrinton LJ, et al. "Incidence and prevalence of inflammatory bowel disease . . . organization, 1996-2002." Am J Gastroenterol. 2008;103(8):1998-2006.
Candès E, et al. "Fast discrete curvelet transforms." Multiscle Model Sim. 2006;5(3):861-99.
Guo K, Labate D. Optimally sparse multidimensional representation using shearlets. SIAM J Math Anal. 2007;39:298-318.
Knoll F, et al. "Fast reduction of undersampling artifacts in radial MR angiography with 3D total variation on graphics hardware." MAGMA. 2010;23(2):103-14.
Freiberger M, et al. "The AGILE library for image reconstruction in biomedical sciences using graphics card hardware acceleration" Computing in Sci & Engineering 2013;15:34-44.
Beck A, Teboulle M. "Fast gradient-based algorithms for constrained total variation image denoising and deblurring problems". IEEE Trans Image Process. 2009;18(11):2419-34.
McCollough CH, et al. The phantom portion of the ACR computed tomography accreditation program: practical tips, artifact examples, . . . avoid. Med Phys. 2004;31(9):2423-42.
Wang Z, et al. "Image quality assessment: From error visibility to structural similarity." IEEE Trans Image Proc. 2004;13(4):600-12.
Kalendar WA. Computed Tomography. 3rd ed. Erlangen, Germany: Publicis Publishing; pp. 1-380, 2011.
Grant, Katherine et al., "SAFIRE: Singogram Affirmed Iterative Reconstruction," IEEE Nuclear Science Symposium,pp. 1-7, 2012.
Benchmark Report CT. IMV 2006 CT Market Summary Report, pp. 1-7.
Kosters, Thomas et al., "EMRECON: An Expectation Maximization Based Image . . . ," 2011 IEEE Nuclear Science Symposium Conference Record, pp. 4365-4368.
www.siemens.com/low-dose, 2013, pp. 1-154.

* cited by examiner

CT dose reduction using compressed sensing (Aim 4)

▫ Exploit image sparsity to reduce number of projections
   ▫ E.g., PICCS technique (Chen GH et al. Med Phys 2008)
▫ Challenge: practical undersampling scheme for multislice CT
   ▫ Modulating mA: slow ✗
   ▫ Modulating kVp: attenuation\ ✗
   ▫ Mechanical beam shutter
      ▫ Incoherence along θ ✓
      ▫ No incoherence along z ✗
   ▫ Moving multihole collimator ✓✓
      ▫ Incoherence along θ and z

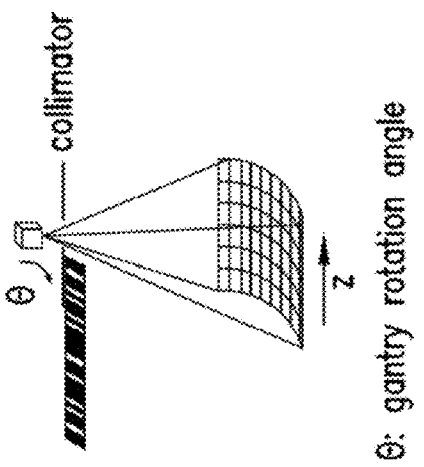

FIG. 8

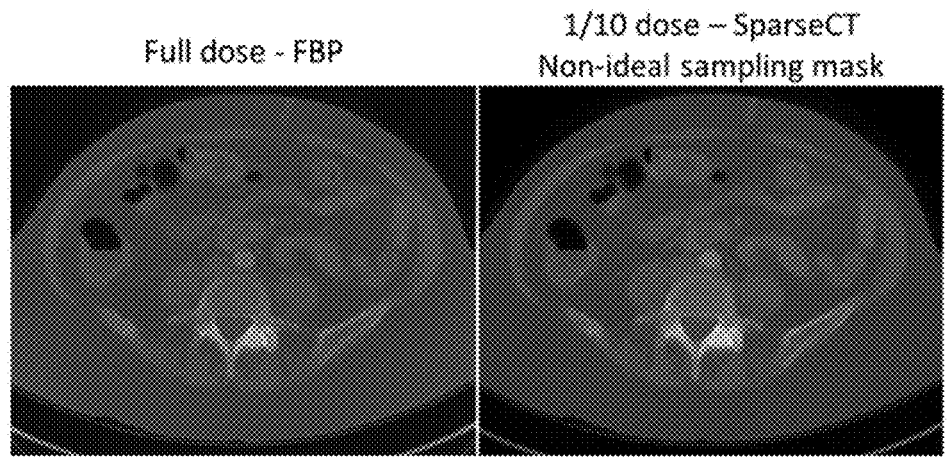
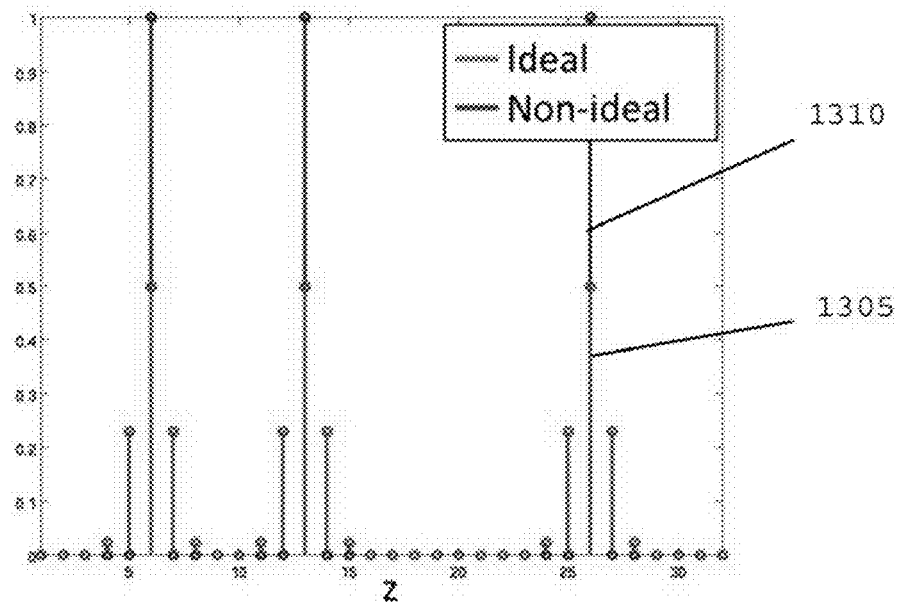
Figure 13

Figure 14
Examination performed at 120-FBP    Examination performed at 100-IR
Figure 15

SYSTEM, METHOD, AND COMPUTER ACCESSIBLE MEDIUM FOR MODULATING X-RAY BEAM INTENSITY

CROSS-REFERENCE TO RELATED APPLICATION(S)

This application is a continuation-in-part and claims the benefit and priority from International Patent Application No. PCT/US2014/031609 filed on Mar. 24, 2014, which claims the benefit and priority from U.S. Provisional Application No. 61/804,415 filed on Mar. 22, 2013, the entire disclosures of which is are incorporated herein by reference in their entirety.

FIELD OF THE DISCLOSURE

The present disclosure relates generally to computed tomography ("CT"), and more specifically, to exemplary systems, methods and computer-accessible medium for modulating x-ray beam intensity in a CT imaging system.

BACKGROUND INFORMATION

Rapidly increasing utilization of X-ray CT has heightened concerns about the collective radiation exposure to the population as a whole, and about potential risks to patients undergoing recurrent imaging for chronic conditions or persistent complaints. These concerns have generated a great deal of attention to practical radiation dose reduction strategies. For example, a recent addition to the commercially-available dose-reduction arsenal is on iterative reconstruction, which uses reduced tube current, and applies nonlinear procedures to denoise the resulting images. However, such approaches can be limited by the minimum useful tube current (e.g., the photon starvation problem), and in practice, only moderate dose reductions of up to about 30-40% below the prior state of the art. Recent advances in detector technology can offer similar reductions.

Radiation exposure has received much attention of late in the medical literature and lay media. It is commonly recognized that computed tomography (CT) has tremendously advanced our diagnostic capabilities broadly throughout medicine. These diagnostic benefits have combined with widespread availability and rapidity of scanning to produce marked increases in CT utilization, estimated at approximately 69 million CT scans per year in the US. However, rapidly increasing utilization has heightened concerns about the collective radiation exposure to the population as a whole, and about potential risks to patients undergoing recurrent imaging for chronic conditions or persistent complaints.

CT has received a lot of scrutiny because of its relatively high radiation dose per exam. While it comprises only about 17% of all medical imaging procedures, it produces approximately half of the population's medical radiation exposure, with nuclear medicine contributing approximately one quarter of the collective dose to the population, and fluoroscopy and conventional x-ray exams accounting for the remainder (See Refs. 5 and 6).

Various strategies have been proposed to reduce radiation exposure to the population as a whole, and to individual patients (See Refs. 7 and 8). Due to challenges of education and dissemination, the most successful and widely implemented dose-reduction measures can be those that perform with little need for end-user optimization. Examples of currently used measures are below.

Exemplary automated tube current modulation: Automated tube current modulation or dose modulation, can adjust the x-ray tube output mAs to the patient's anatomy in order to maintain a desired level of image quality (See Refs. 10 and 11). Greater mAs can be used in areas with greater x-ray attenuating path-lengths such as the shoulders or the pelvis, and lower mAs can be used in regions containing less attenuating material such as the lungs.

Adaptive Collimation: The development of wider detector arrays facilitating rapid anatomic coverage has had the unintended consequence of increasing z-overscanning, in which the anatomy above and below the desired scan range can be inadvertently irradiated. Implementation of adaptive collimators that open and close asymmetrically as the patient can be moved through the gantry can mostly eliminate this z-overscanning, with dose savings on the order of 10-35%, depending on the detector configuration and scan length (See Ref. 12).

Iterative Reconstruction: Iterative reconstruction procedures can solve an optimization problem (See Ref. 13) in which the cost function can be designed to reduce noise or artifacts resulting from reductions in x-ray tube current. Iterative reconstruction procedures can transform back and forth between the raw data "projection-space" and the image domain with each iteration, but, as this approach can be computationally expensive, most manufacturers have implemented more rapid shortcut procedures designed to achieve similar ends. Implementation details vary between manufacturers, but generally involve a variety of procedures to shift some of the iterative "correction steps" into the raw data or image domains, combined with advanced modeling of the CT acquisition system, and nonlinear image filtering, to reduce noise in homogeneous regions while attempting to preserve anatomic edge information. The noise reduction effected by iterative reconstruction techniques can enable substantial reductions in radiation exposure. The somewhat different noise texture of the resultant images can need some acclimatization on the part of radiologists, but in practical routine clinical use, dose reductions on the order of 20-40% can be typical (See Ref. 16).

Reduced kVp imaging: In many applications, reduced kVp can result in substantial dose savings. The greatest benefits can be realized in vascular imaging applications, as iodine attenuates lower energy x-rays more strongly than higher-energy x-rays. Adoption of low kVp approaches has been hastened through approaches such as CarekV which can direct the CT scanner to select the kVp setting that can result in the lowest dose to the patient, while meeting user-selected image quality constraints and inherent x-ray tube output limits.

Detector technology advances: CT manufacturers have spent substantial effort optimizing the materials (e.g. Siemens UFC detectors) and construction of their detector elements to maximize the conversion of incident x-rays to meaningful signal. Most recently, analog to digital conversion functionality has been moved to chips located on the detector elements themselves (e.g., Siemens Stellar detectors), thus reducing electronic noise. This has been shown to permit dose reductions on the order of about 30%.

Each of the dose reduction strategies above has the potential to reduce a dose incrementally from previous techniques. Some of these techniques may only be appropriate in select circumstances (e.g. dose reductions from tube current modulation for small patients and low kVp for vascular imaging particularly in smaller patients). In other cases, multiple techniques can be used in combination, producing multiplicative dose saving effects (See Ref. 18)

(e.g. four 30% dose reduction strategies can in principle be used in combination to effect a 76% dose reduction relative to the starting point). However, existing methods cannot achieve routine submillisievert scanning in the majority of patients, and submillisievert scans remain elusive in almost all abdominal applications. Signature low dose results often involve small patients scanned at low kVp in the chest (e.g., where inherent x-ray attenuation can be low), but doses can be substantively higher in the abdomen and for typical patient sizes.

An alternative approach to reduce radiation dose in CT is the application of compressed sensing ("CS") techniques (See Refs. 19 and 20). CS can exploit image compressibility to reconstruct an image with full information from a reduced set of incoherent measurements sampled below the Nyquist-Shannon rate. The reconstruction can also be iterative, but in contrast to the iterative reconstruction techniques mentioned above which denoise the fully-sampled images acquired with lower tube-current, the cost function can be designed to enforce sparsity in the space where the image can be compressible. Significant reductions in the number of measurements can be accomplished if the image can be sparse in a known transform domain (e.g., sparsity condition) and if the resulting aliasing artifacts can add incoherently to the sparse image representation (e.g., incoherence condition). CT presents favorable conditions for the application of CS since (a) medical images are naturally compressible by various transforms which lead to sparse representations, and (b) discarding projections can result in low-value streaking artifacts that add incoherently to the image representation.

Some current radiation dose reduction techniques in CT can rely on techniques to reduce the x-ray tube output throughout the CT scan acquisition (e.g., without rapid modulations). In some cases, nonlinear reconstruction techniques (e.g., iterative reconstruction or nonlinear filtering methods) can be used to reduce noise in the resulting images. However, there are currently no CT techniques that can undersample the x-ray projection data itself, which can be essential for making effective use of techniques such as compressed sensing to further reduce CT radiation dose beyond current limits. Thus, it may be beneficial to provide an exemplary system, method, and computer accessible medium that can modulate x-ray beam intensity for use with CS reconstruction, and which can overcome at least some of the deficiencies described herein above.

SUMMARY OF EXEMPLARY EMBODIMENTS

Exemplary system, method and computer accessible medium according to an exemplary embodiment of the present disclosure can facilitate orders of magnitude radiation dose reductions in CT. While current radiation dose reduction techniques in CT can rely on techniques to reduce the x-ray tube output throughout the CT scan acquisition, the exemplary system, method and computer accessible medium can utilize nonlinear reconstruction techniques to reconstruct images with full image quality, information content and diagnostic utility from undersampled datasets, in which a significant fraction of x-ray exposures have been eliminated.

These and other objects of the present disclosure can be achieved an exemplary imaging system that can include, for example, a source first arrangement that can provide x-ray radiation, and a collimator second arrangement that can be provided in a path of the x-ray radiation, and can be configured to undersample the radiation which can be forwarded to the portion(s) of the anatomical structure. A third hardware arrangement can be configured to receive a further radiation from the portion(s) that can be based on the undersampled radiation.

In certain exemplary embodiments of the present disclosure, the collimator second arrangement can include a multi-hole collimator, which can be configured to move in such a way that different pathways between the source first arrangement and the third arrangement are blocked or left unobstructed at different times. The collimator second arrangement can be moved by a piezoelectric drive, a stepper motor or a pneumatic drive. The second arrangement can be further configured undersample the radiation, and provide resultant radiation to the portion(s) of an anatomical structure that can be based on the collimated radiation, and the third arrangement. A hardware fourth arrangement can be configured to generate an image(s) of the portion(s) using a compressed sensing reconstruction procedure, or other suitable reconstruction procedure, as a function of the resultant radiation.

In certain exemplary embodiments of the present disclosure, the system can further include a gantry bore and a gantry table located in the gantry bore, and the source first arrangement can be located on the gantry bore. The collimator second arrangement can be configured to reduce a number of the radiations along a detector array fan or cone angle between the source first arrangement and the third arrangement. The second arrangement can be further configured to undersample the radiation, and provide resultant radiation to the portion(s) of the anatomical structure that can be based on the undersampled radiation, and an imaging fourth arrangement can be configured to receive further radiations from the portion(s), and generate an image(s) of the portion(s) based on the further radiations. In certain exemplary embodiments of the present disclosure, the source first arrangement and the third arrangement can be part of a multislice computed tomography ("CT") scanner.

In a further exemplary embodiment of the present disclosure can be an imaging system, which can include, for example, a source first arrangement that can be configured to provide an x-ray radiation, a multi-hole collimator second arrangement, and a hardware third arrangement. The second and third arrangements can be provided in a path of the radiation, and the second arrangement can be provided between the first and third arrangements.

In a further exemplary embodiment of the present disclosure can be a system, method and computer-accessible medium for imaging a portion(s) of an anatomical structure that can include, for example moving a multi-hole collimator arrangement in and out of a path of an x-ray radiation provided by an x-ray source arrangement; the path can extend to or through a radiation receiving arrangement. An image of the portion(s) can be generated based on further radiation received from the portion(s) by the radiation receiving arrangement using a compressed sensing reconstruction procedure. The further radiation can be associated with the x-ray radiation. The image can be generated using an inverse problem solution algorithm incorporating a sparsity transform, which can include wavelets, finite differences, curvelets, or other elements known in the art.

In a further exemplary embodiment of the present disclosure, an apparatus can be provided that can include a multi-hole collimator arrangement configured to undersample an x-ray radiation provided from a source arrangement. The particular undersampled pattern can different at adjacent angles of a gantry bore.

In a further exemplary embodiment of the present disclosure is an exemplary system, method, and computer-accessible medium for generating an image(s) of a portion(s) of an anatomical structure including incoherently interrupting an x-ray radiation provided by an x-ray source arrangement that is directed at the at least one portion to generate a resultant x-ray radiation having a particular undersampled pattern, receiving, at a radiation receiving arrangement, the resultant x-ray radiation provided from the portion(s), and generating the image(s) of the portion(s) based on the resultant x-ray radiation received at the radiation receiving arrangement These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features, and advantages of the present disclosure will become apparent from the following detailed description taken in conjunction with the accompanying Figures showing illustrative embodiments of the present disclosure, in which:

FIG. 8 is an exemplary image illustrating a comparison of conventional imaging techniques and the exemplary compressed sensing technique according to an exemplary embodiment of the present disclosure;

FIG. 12 is a set of images illustrating filtered back-projection reconstruction of fully-sampled in vivo abdominal data (e.g., full dose) and SparseCT reconstruction of 10-fold retrospectively undersampled data (e.g., ¹/₁₀ dose) according to an exemplary embodiment of the present disclosure;

FIG. 13 is a graph illustrating a non-ideal and an ideal sample patter for the exemplary SparseCT construction according to an exemplary embodiment of the present disclosure;

FIG. 14 is an image of the expectation maximization reconstruction of fully-sampled in vivo abdominal data according to an exemplary embodiment of the present disclosure;

FIG. 15 is a set of images showing a comparison of CT enterography images with traditional and reduced radiation dose using commercially available dose-reduction methods according to an exemplary embodiment of the present disclosure.

Figure 1C:
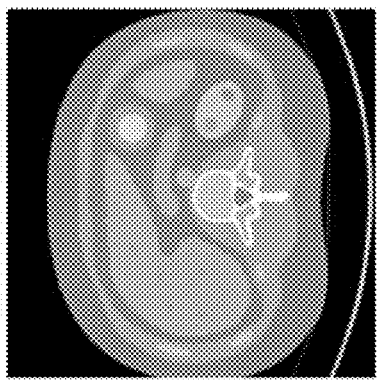
FIGS. 1A-1C are exemplary images generated with three distinct reconstruction methods: A) traditional filtered back protection, B) SAFIRE, a commercial iterative reconstruction, with tube current reduced uniformly to yield ⅛ the radiation dose of the traditional case, and C) use of the exemplary system, method, and computer-accessible medium according to the present disclosure to reconstruct an image from an undersampled dataset omitting ⅞ of the traditional projections and corresponding to ⅛ the radiation dose of the traditional case.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures or the appended claims.

DETAILED DESCRIPTION OF EXEMPLARY EMBODIMENTS

The exemplary system, method, and computer-accessible medium according to an exemplary embodiment of the present disclosure can be used for rapid and incoherent interruption of the x-ray source on the CT gantry which, when combined with exemplary sparsity-based CS reconstruction procedures, can enable reconstruction of high-quality images from a markedly reduced number of projections. In particular, various methods can be used to interrupt the x-ray source including an exemplary multi-hole collimator and/or an exemplary pulsed x-ray tube.

Previous CS techniques suggested the reconstruction of an image from a reduced number of radial projections, and subsequent work further explored this idea using real CT data (See Ref. 21). Recent work has also demonstrated, in simulations, that reducing the number of projections can achieve a higher radiation dose reduction than reducing the tube current (See Ref. 22).

Figure 1B:
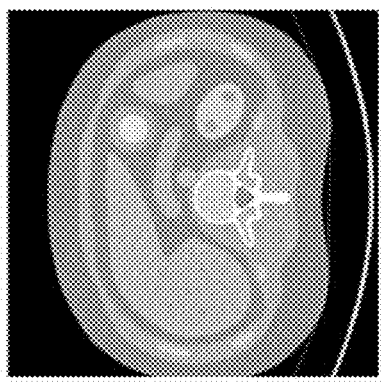
Figure 1A:

In contrast to previous work, which was not effective in reducing radiation dosages, FIGS. 1A-1C show experimental results demonstrating (i) the improved performance of sparse reconstruction with incoherent undersampling as compared with state-of-the-art iterative reconstruction with reduced tube current using the exemplary system, method, and computer-accessible medium and (ii) favorable comparisons in vivo between an exemplary full-dose study and a simulated tenfold-reduced-dose study with a realistic undersampling model and SparseCT reconstruction.

In Magnetic Resonance Imaging (MRI), CS using angularly-undersampled radial k-space acquisitions, has enabled orders-of-magnitude accelerations without degradation of MR image quality (See Ref. 28). Radial MRI and CT share similar data acquisition schemes, and therefore, similar orders-of-magnitude undersampling factors can be expected in CT, which can lead to the target sub-mSv acquisitions in all parts of the body. One additional advantage of CS approaches can be that they can be largely complementary to existing dose reduction approaches, and can be used in combination with other exemplary technique for greater improvements.

Exemplary incoherent undersampling procedure can be a key to unlocking the benefits of CS for CT. Two exemplary procedures of incoherent undersampling can be employed: (a) exemplary moving multi-hole collimators, and (b) exemplary pulsed X-ray tube designs. Moving collimators in particular, and potentially pulsed X-ray tubes as well, can be able to be implemented as a modular hardware upgrade which, together with software upgrades to reconstruction procedures, can be deployed on existing CT systems, thereby significantly expanding the impact of the work, and facilitating rapid and broad dissemination of the method. Tailored sparsity-enforcing compressed-sensing reconstruction procedures can be utilized to take maximal advantage of the resulting undersampling.

The exemplary system, method, and computer-accessible medium, according to an exemplary embodiment of the present disclosure, can enable orders-of-magnitude rather than incremental dose reductions, which can represent a game-changing strategy in CT dose reduction methods. The exemplary system, method, and computer-accessible medium can be broadly applicable to all anatomy from head to toe, and can also be used in combination with existing approaches for further dose reductions.

Exemplary Image Reconstruction Framework

Exemplary image reconstruction procedures can be used to enforce sparsity subject to data consistency constraints. Given the acquisition model y=Ax, where y can be the undersampled set of projections, A can be the acquisition matrix or forward model which can include the scanner geometry, and x can be the image to reconstruct, the reconstruction for the exemplary system, method, and computer-accessible medium can be given by, for example:

$$\min_{x} \|Ax - y\|_2^2 + \lambda \|Tx\|_1, \quad (1)$$

where T can be a sparsifying transform under which x can have a sparse representation, and λ can be a regularization parameter that can weight the contribution of the sparsity-term (e.g., right-hand term) relative to the data consistency term (e.g., left-hand term). Various procedures can be used to solve Eq. (1) in a very efficient way using, for example, non-linear conjugate gradient, iterative soft-thresholding, and/or gradient-descent methods.

Figure 2A:
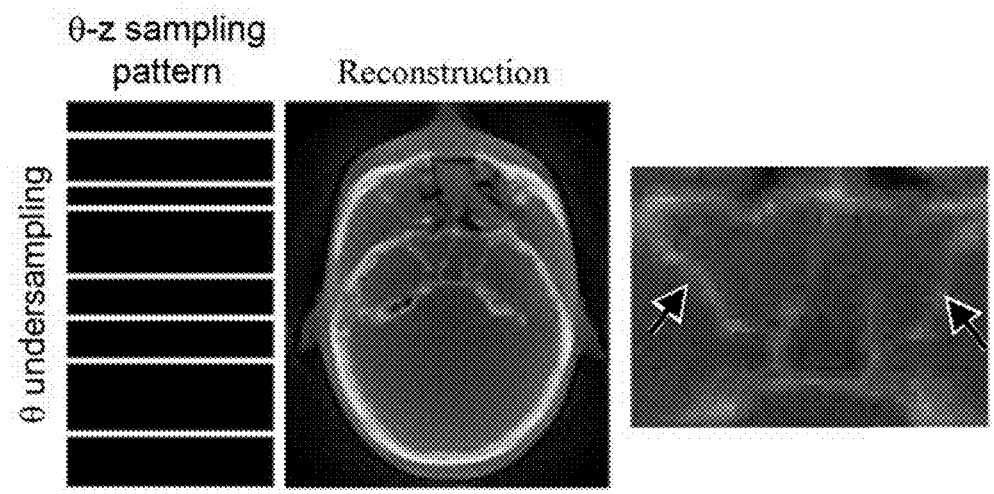
FIGS. 2A and 2B are exemplary images of θ-only undersampling and θ-z undersampling according to an exemplary embodiment of the present disclosure.

Much of the existing work on sparse reconstruction for CT has employed decimated parallel-beam data (e.g., for an undersampling factor of R, only every Rth projection can be used). This exemplary theoretical model can be useful to show proof of concept, but this type of rapid x-ray beam interruption at frequencies on the order of 1-5 kHz can be impossible with current X-ray tube and scanner designs, and thus does not take into account realistic scanner geometries. First, realistic scanner geometry can be included. Assuming a multislice CT scanner geometry, the most straightforward undersampling pattern can eliminate data at selected gantry rotation angles θ (e.g., θ undersampling). Second, as multiple slices along the z-axis (e.g., cone-beam direction of the detector array) can be acquired for each θ, an improved undersampling pattern can be used, where a different subset of z-axis positions can be irradiated by the incident x-ray beam for each gantry rotation angle, resulting in a θ-z undersampling pattern (e.g., FIG. 2A). The subset of z-slices for each θ angle can be chosen randomly to maximize incoherence. This type of undersampling pattern can be analogous to an exemplary undersampling pattern for dynamic MRI studies, where a different radial k-space undersampling pattern can be used for each time point (See Ref. 28), if the time-dimension is replaced with the slice-dimension.

Figure 2B:
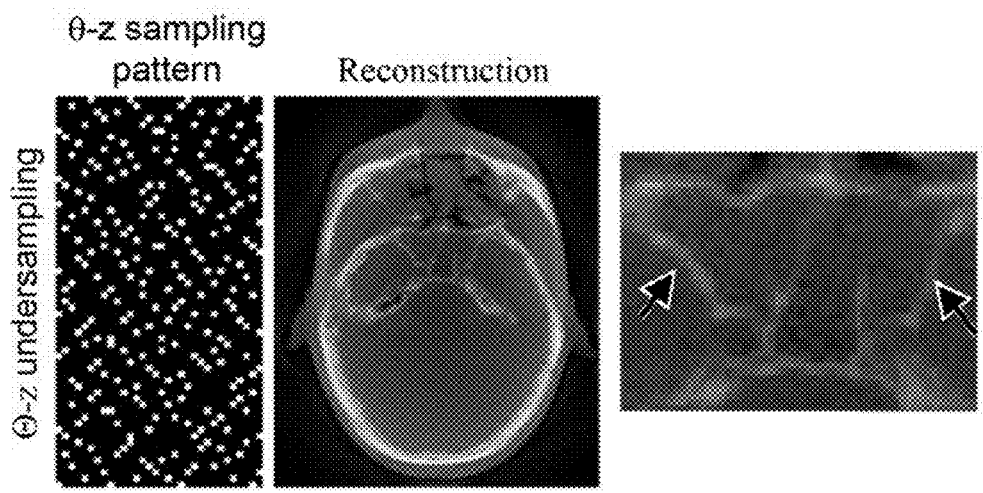

Higher-dimensional undersampling patterns can present favorable conditions for compressed sensing since aliasing artifacts can be effectively distributed over a larger space with lower-intensity, and sparsity can be exploited along the extra dimensions (See Refs. 19 and 23). In CT, θ-z undersampling can distribute artifacts incoherently throughout the full three-dimensional ("3D") data volume, thereby improving performance. In order to compare the performance of θ-only undersampling and θ-z undersampling, an 8-fold undersampling factor on numerical phantom data generated can be simulated using sequentially-acquired (e.g., non-helical) cone-beam geometry (e.g., FIG. 2B). The fully-sampled data set included 800 projections and 192 slices. The matrix A was given by the forward operator of the FDK reconstruction procedure (See Ref. 29). Sparse reconstruction was performed using 3D-wavelets (e.g., 4-tap, Daubechies basis functions) as the sparsifying transform. As can be seen, θ-z undersampling improves performance as compared with θ-only undersampling, due to the increased incoherence, and the ability to exploit extra sparsity along the slice dimension. Based on the above, the θ-z undersampling approach can be used for the exemplary system, method, and computer-accessible medium, which can be implemented using the moving multi-hole collimator described below.

Exemplary Results

The exemplary system, method, and computer-accessible medium can be compared against Sinogram Affirmed Iterative Reconstruction ("SAFIRE"), a state-of-the-art reduced-tube-current technique employing iterative reconstruction and provided by Siemens Medical Solutions on its commercial CT scanners. Data for the comparison were generated from phantom experiments performed on a Siemens SOMATOM Definition Edge CT scanner using a step and shoot protocol. Comparison was performed using a high dose-reduction factor (e.g., 8-fold or about 87.5% reduction in this case, which can be much higher than the usual 20-30% used in typical clinical scans) in order to demonstrate more-than-incremental gains enabled by the exemplary system, method, and computer-accessible medium. SAFIRE data were acquired with tube-current of about 25 mAs and reconstruction was performed online on the scanner. To simulate the exemplary system, method, and computer-accessible medium undersampling, images acquired by sampling fully at about 200 mAs were forward projected, and retrospectively undersampled, using the θ-z undersampling pattern described above. The forward and adjoint acquisition operator were implemented in the EMrecon software package (See Ref. 30) which can support the use of full cone beam projections. Reconstruction for the exemplary system, method, and computer-accessible medium was performed using 3D finite differences as the sparsifying transform, which can be equivalent to minimization of 3D total variation. The reconstruction procedure can enforce data consistency in the original cone-beam space.

Figure 3:
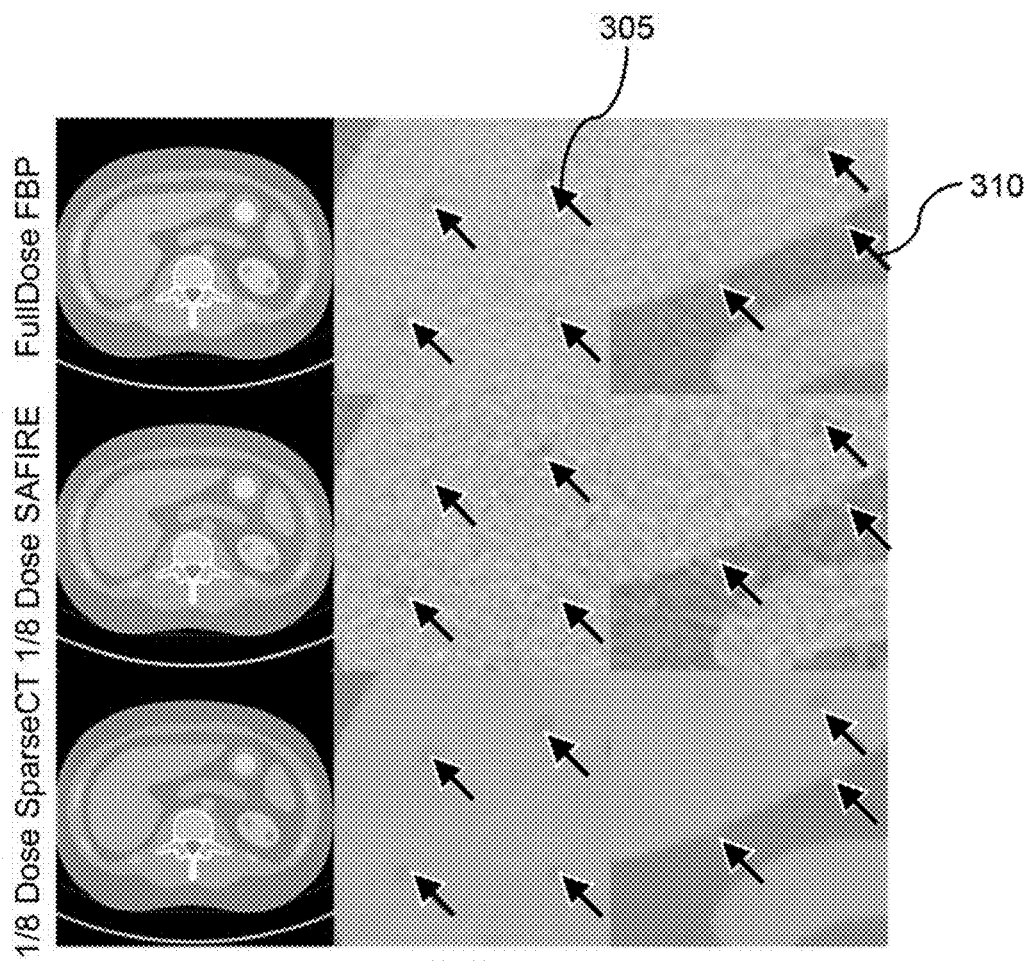
FIG. 3 is a set of images illustrating reconstruction of phantom data according to an exemplary embodiment of the present disclosure.

FIG. 3 is a set of images illustrating reconstruction of phantom data acquired with full dose (e.g., 200 mAs, no undersampling) using filtered-back projection ("FBP"), an 8-fold reduced tube-current (e.g., 25 mAs, no undersampling) using SAFIRE, and an 8-fold retrospective undersampling (e.g., 200 mAs, 8-fold θ-z undersampling) using the exemplary system, method, and computer-accessible medium. The leftmost column shows full field of view reconstructions and the columns on the right show zoomed panels to emphasize the preservation of small features (305) and low-contrast features (310) in the exemplary system, method, and computer-accessible medium compared to the exemplary system, method, and computer-accessible medium. FIG. 3 illustrates he higher reconstruction performance of the exemplary system, method, and computer-accessible medium in comparison to SAFIRE, particularly in the preservation of high-resolution and low-contrast features, which can be buried in the residual noise of the SAFIRE reconstruction. The nonlinear reconstruction in the exemplary system, method, and computer-accessible medium can also denoise the reconstructed images, presenting superior performance even compared with the full-dose FBP reconstruction, which can be a linear reconstruction approach. This can be due to the fact that the phantom can consist of piece-wise smooth features with truly sparse representations in the finite difference domain, and consequently can enable improved compressed sensing reconstructions.

Exemplary Reconstruction of In Vivo Data and Compensation for Non-Ideal Sampling Patterns Exemplary reconstruction of an in vivo abdominal dataset can also be shown, which can present realistic anatomy with more challenging structures and more highly textured features than from a phantom from FIG. 3. A compensation approach can also be used for non-ideal sampling patterns in the exemplary reconstruction procedure. Passage of the incident beam through the collimator holes can result in partial blockage of some detector-rows due to beam profile deformations and/or focal spot blurring. These effects can be included in the reconstruction procedure by using a non-binary (e.g., continuous) sampling mask in the acquisition matrix A (Eq. (1)), which weights the reconstruction results in cone-beam data space to improve data consistency, and to ensure that all incident photons are used in the reconstruction, maximizing dose efficiency (C3,A3).

FIG. 12 is an image that shows the reconstruction of in vivo abdominal data with retrospective 10-fold undersampling (e.g., an order-of-magnitude dose reduction) using the exemplary SparseCT with compensation for non-binary sampling mask. The results are similar in quality to those for conventional FBP reconstruction of the fully-sampled data. Some slight degradations in small structures were noted, but these structures can be preserved robustly by suitable optimizations of the sparsifying transform and the regularization parameter. For example, the 3D total variation transform used can be replaced with an exemplary wavelet or curvelet transform that can enhance sparsity in the presence of gradual intensity variations. Thus, the exemplary system, method and computer-accessible medium, according to an exemplary embodiment of the present disclosure, illustrates: i) high-quality reconstruction of in vivo data, (ii) the potential for order-of-magnitude dose reduction and (iii) compensation for non-ideal sampling patterns. The exemplary non-binary sampling mask, which can be non-ideal (e.g., line 1305 of FIG. 13) can be assumed to be the convolution of the binary sampling pattern, for example, ideal (e.g., line 1310 from FIG. 13) by a Gaussian kernel along the slice dimension (e.g., the detector-row dimension) to represent the blurring effects of the collimator holes on the beam profile. An exemplary undersampling model, incorporating the detailed physics of beam interruption can be developed. When using the exemplary multi-hole collimator, the effective sampling mask can be measured using a phantom experiment and then used for subsequent scans with similar dose reduction factors.

Exemplary Gaussian-Noise Vs. Poisson-Noise Statistics

The in vivo abdominal dataset from FIGS. 12 and 13 can also be reconstructed using an expectation maximization ("EM") to consider CT noise statistics (e.g., shot-noise, Poisson distribution). The results can be essentially indistinguishable from those in FIGS. 12 and 13. For example, FIG. 14 shows an EM reconstruction of the fully-sampled data, for comparison with the leftmost image in FIG. 12. For sufficient baseline SNR, images can usually be very compressible and the performance of compressed sensing may not be highly sensitive to the particular noise model. Thus, the use of EM can provide an advantage in cases with low SNR, for example, for data acquired with reduced tube-current, which can require explicit knowledge of the noise distribution to perform denoising in the reconstructed images Comparative Evaluation of Image Quality for Dose Reduction in Crohn's Disease Crohn's disease ("CD") is a common entity with a prevalence of approximately 26 to 198.5 cases in 100,000 persons. CT enterography ("CTE") is the study of choice for the diagnosis of Crohn's disease and for evaluation of various complications. The disease affects patients in a bimodal age distribution with many young patients undergoing multiple CTE examinations, making cumulative radiation exposure an important issue. In a recent retrospective study, image quality and dose reduction in 50 patients undergoing CTE was compared with advanced commercially available dose reduction techniques (e.g., lower mAs, 100 kVp, and iterative reconstruction) with their prior imaging performed with a standard acquisition scheme (e.g., 200 mAs. 120 kVp, and filtered back projection reconstruction). Two readers blind to the acquisition procedure independently evaluated the examinations for overall image quality, bowel wall sharpness, mesenteric vessel clarity, and presence of artifact. These categories were scored on a 1 to 5 scale with 5 being optimal.

The results of the exemplary study showed that there was no statistically significant difference in various measures of image quality with iterative reconstruction techniques ("IR". for both readers (see e.g., Table 1 and FIG. 15) when compared to the standard FBP. The average radiation dose for the IR was significantly lower than for the FBP (e.g., CTDIVol 9.95±3.83 versus 15.00±5.57; $p<0.0001$) resulting in radiation dose reduction of approximately 33%.

TABLE 1

Results of CTE image quality comparison study.

| | Reader 1-FBP | Reader 1-IR | Reader 2-FBP | Reader 2-IR |
|---|---|---|---|---|
| Overall Quality | 3.92 ± 0.83 | 4.04 ± 0.75 | 4.96 ± 0.20 | 4.49 ± 0.41 |
| Bowel Wall Sharpness | 4.12 ± 0.69 | 4.22 ± 0.84 | 4.92 ± 0.27 | 4.57 ± 0.48 |
| Mesenteric Vessel Clarity | 4.04 ± 0.75 | 4.34 ± 0.85 | 4.94 ± 0.24 | 4.64 ± 0.45 |
| Artifact | 3.68 ± 0.55 | 3.78 ± 0.46 | 3.24 ± 0.52 | 3.49 ± 0.41 |

Figure 16A:
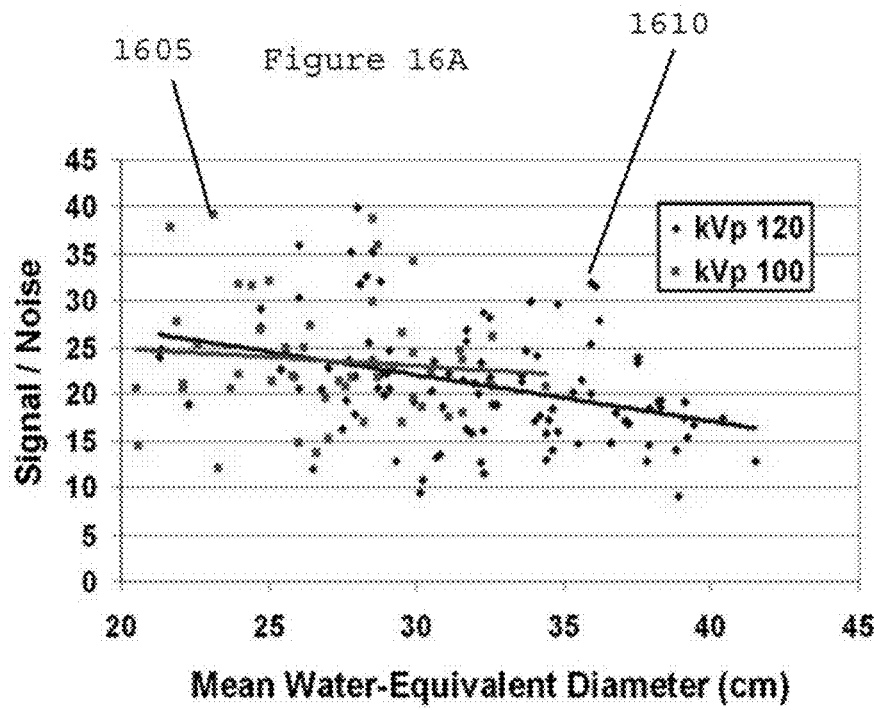
FIGS. 16A and 16B are graphs of measured signal-to-noise-ratio and CTDIvol as a function of subject size in a study of pulmonary angiography according to an exemplary embodiment of the present disclosure.
Figure 16B:
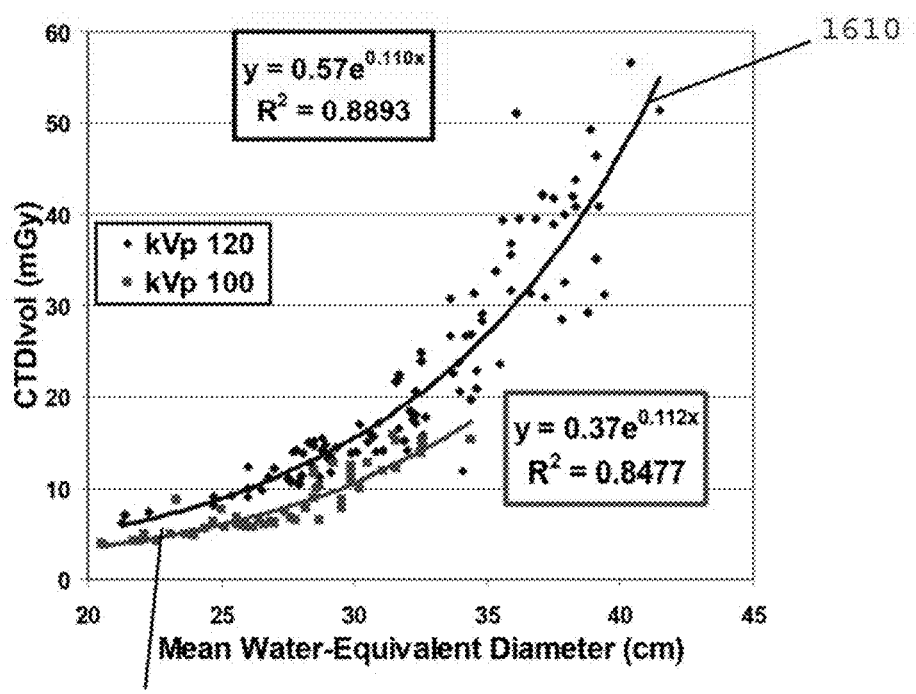

Comparative Evaluation of Image Quality for Dose Reduction in Pulmonary Angiography The effectiveness of radiation dose reduction in the setting of pulmonary angiography was also examined. FIGS. 16A and 16B are graphs that show results from an exemplary study documenting radiation exposure and quantitative measures of image quality as a function of patient size using a combination of automated tube current modulation and 100 kVp imaging for CT pulmonary angiograms. Main pulmonary artery CTDIvol is shown as a function of mean water-equivalent diameter at 100 kVp (e.g., element 1605) and 120 kVp (e.g., element 1610), with superimposed exponential fit curves and fit equations. CTDIvol varies substantially with patient size as expected using tube current modulation. 100 kVp and 120 kVp scan protocols using optimized IV contrast infusion procedures were compared using quantitative measures of image quality and radiation dose. In sufficiently small patients, the 100 kVp protocol was found to reduce radiation dose by 33% (e.g., p<0.0001) despite a concurrent 33% decrease in administered IV contrast material, while preserving measured image quality (e.g., p=0.99, signal to noise ratio define.

Exemplary Collimator Arrangement

The exemplary system, method and computer accessible medium, according to an exemplary embodiment of the present disclosure, can mechanically disrupt an x-ray beam close to the x-ray source, which can be in, or adjacent to, an x-ray collimator arrangement. For example, near the source, the x-ray beam can be narrowly confined such that very slight linear motions of a heterogeneously attenuating structure can effectively modulate the x-ray beam intensity at a high frequency as compared to the standard CT gantry rotation time.

Figure 4:
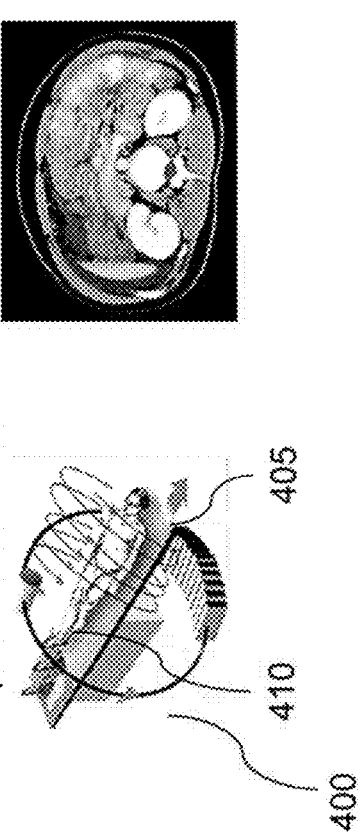
FIG. 4 is an exemplary illustration of an exemplary compressed sensing system according to an exemplary embodiment of the present disclosure.

As shown in FIG. 4, the z-axis can be the position of a CT table 405 and a patient 410 (e.g., from head to foot) normal to the gantry bore, and the gantry angle $\theta$ can be 0° zero when the x-ray source can be above the CT table 405, and 180° when the x-ray source can be below the CT table 405. Using a multislice CT scanner 400 using which x-ray attenuation data can be acquired from several slices per rotation, a moving multi-hole collimator can be utilized, which can expose a different subset of z-axis slices per gantry rotation angle, and thus create an incoherent undersampling pattern along $\theta$ and z.

Figure 5B:
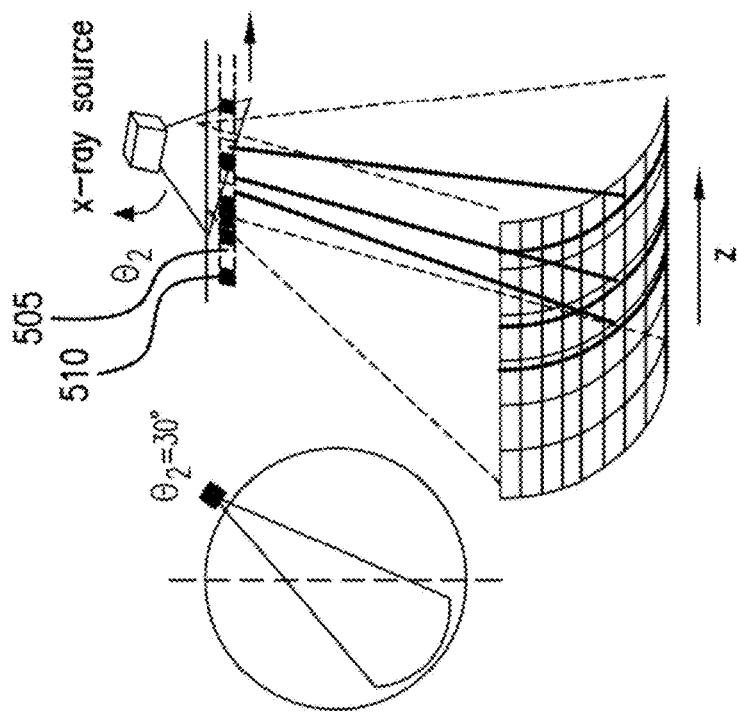
FIGS. 5A and 5B are exemplary schematics illustrating movement of an exemplary collimator arrangement according to an exemplary embodiment of the present disclosure.
Figure 5A:
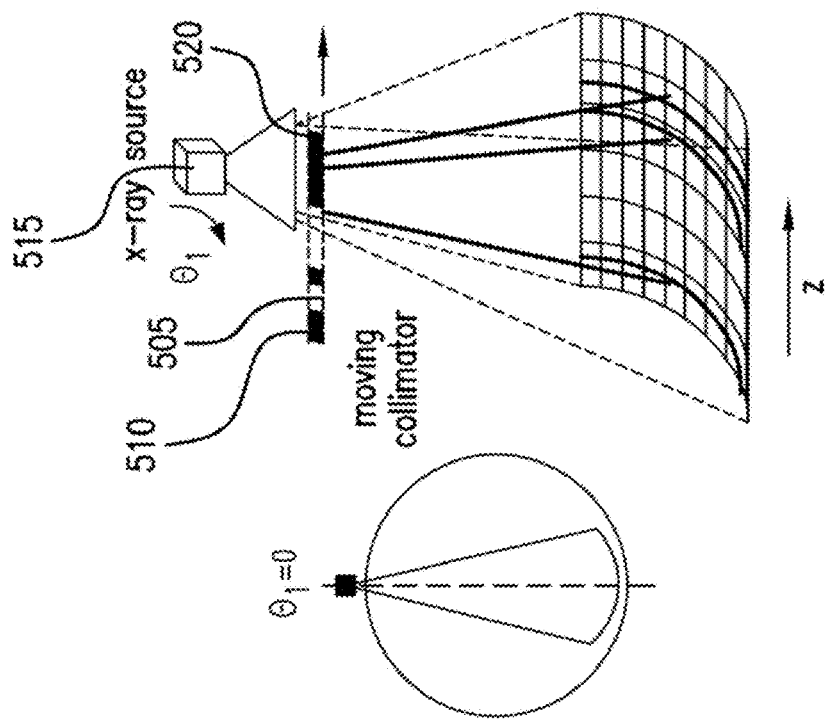

FIGS. 5A and 5B are schematics illustrating movement of the exemplary collimator arrangement (e.g., a moving multi-hole collimator 520 for $\theta$-z incoherent undersampling). The multi-hole collimator 520 can be mounted on the standard fixed collimator housing and needs only linear motion. As the gantry rotates, for example, from $\theta_{1=0}°$ (FIG. 5A) to $\theta_{2=30}°$ (FIG. 5B), the multi-hole collimator 520 can move linearly along the z direction, exposing a different subset of slices at each gantry rotation angle $\theta$. Different slices can be irradiated at adjacent gantry angles, yielding the exemplary $\theta$-z undersampling pattern in FIG. 3. For example, in FIGS. 5A and 5B, a particular pattern of x-ray radiation can be emitted (e.g., the areas denoted by element 505 can facilitate the passing of x-rays while the areas denoted by element 510 can facilitate the blocking of the x-rays).

Figure 6:
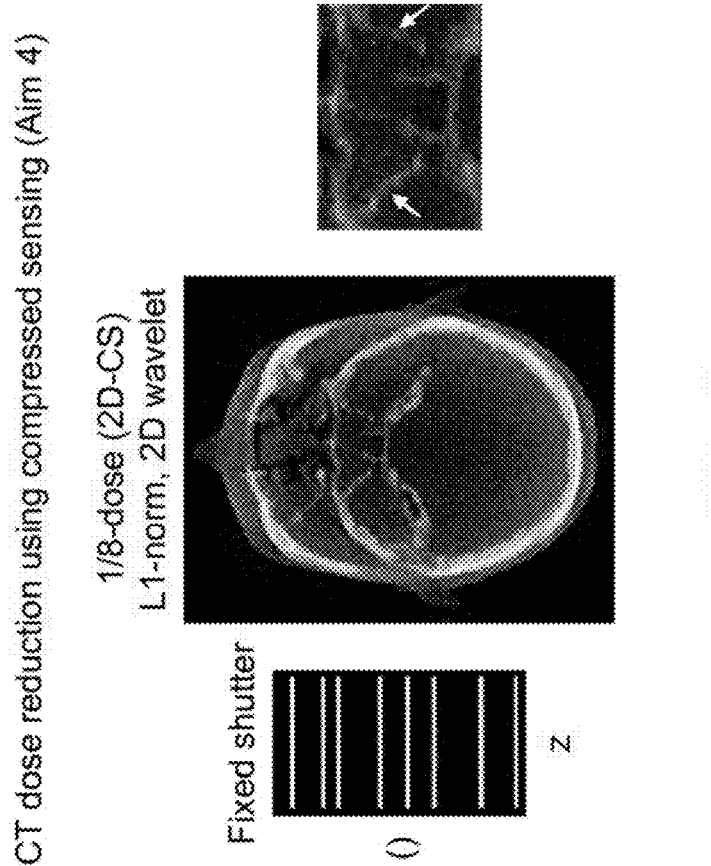
FIG. 6 is an exemplary image illustrating further exemplary results provided by the exemplary compressed sensing system according to an exemplary embodiment of the present disclosure.
Figure 7:
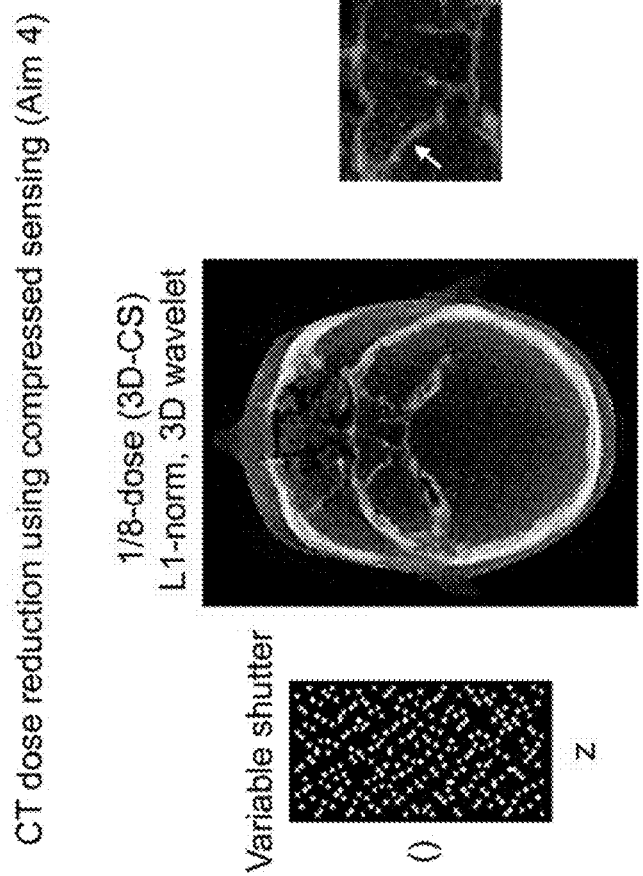
FIG. 7 is an exemplary image illustrating further exemplary results provided by the exemplary compressed sensing system according to an exemplary embodiment of the present disclosure.

This exemplary undersampling pattern can result in a different complement of radial protections for each z-axis position, and can enable a full 3D compressed sensing reconstruction, which can have improved performance over 2D compressed sensing due to increased incoherence and sparsity. (See e.g., exemplary results shown in FIGS. 6 and 7). Image reconstruction can be performed by utilizing 3D image sparsity using a 3D transform (e.g., wavelets, finite differences, and curvelets).

The exemplary system, method and computer accessible medium, according to exemplary embodiments of the present disclosure, can interrupt the x-ray output at the x-ray source 515, including exemplary source collimator designs that can incoherently reduce the number of x-ray projections along the detector array fan angle$\Phi$(See e.g., FIG. 4), which can create an additional undersampling dimension by exposing different detector element combinations within each slice. Using the exemplary system and method, the incoherent undersampling in the (e.g., $\theta$, $\Phi$, z) space can facilitate orders of magnitude reductions in radiation exposure without any effect on the CT image quality.

The exemplary system, method and computer accessible medium, according to exemplary embodiments of the present disclosure, can move the multi-hole collimator 520 via, for example, a piezoelectric drive, a stepper motor, a pneumatic drive, or other similar drive mechanisms. The incident x-ray flux can be reduced at the x-ray source 515, which can result in a diminished radiation exposure to the patient. The exemplary system, method and computer accessible medium can also be fully compatible with and/or utilize commonly used dose-reduction technologies (e.g., including z-axis and in-plane tube current modulation, reduced kVp imaging, adaptive collimation and/or other hardware and software methods currently in use), facilitating multiplicative dose reductions by capturing the benefits of multiple imaging techniques simultaneously.

As shown in FIG. 8, a comparison is provided of conventional imaging techniques and the exemplary compressed sensing technique according to an exemplary embodiment of the present disclosure, can have an incoherence along both $\theta$ and z, while conventional imaging techniques likely cannot achieve incoherence along both $\theta$ and z.

Exemplary Pulsed X-ray Tubes

Figure 9:
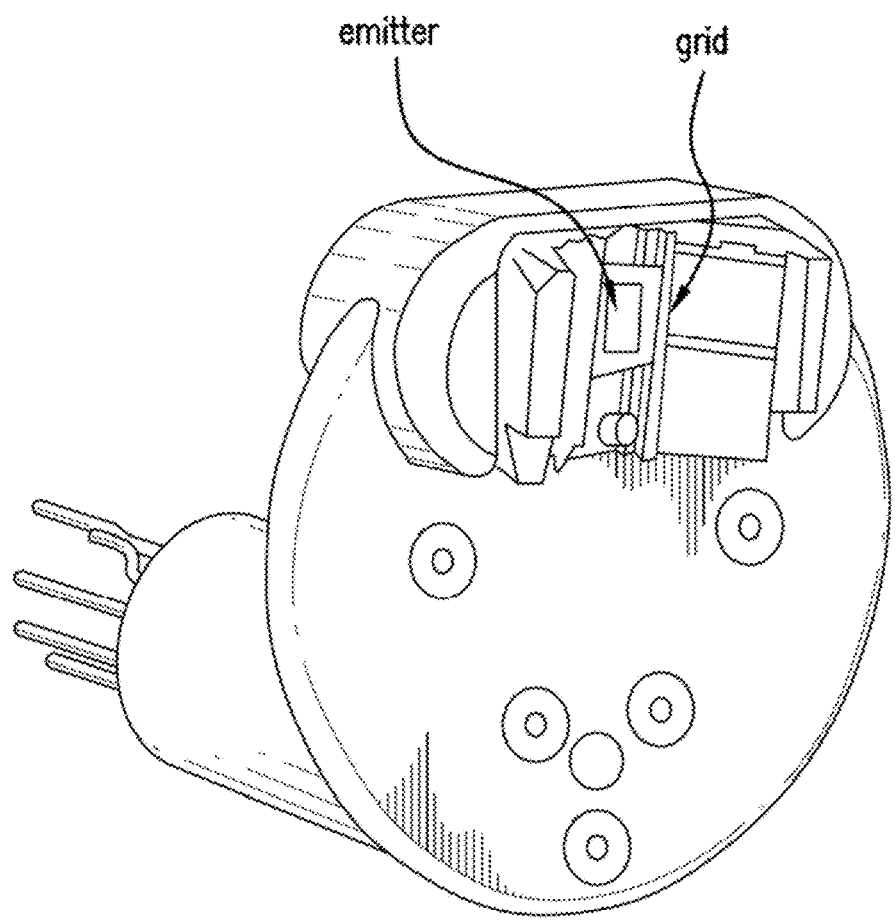
FIG. 9 is an image of an exemplary pulsed x-ray tube according to an exemplary embodiment of the present disclosure.

The x-ray radiation can also be interrupted by pulsing the beam itself at its exemplary source, for example, by turning the source on and off in a desired undersampling pattern (e.g., using the exemplary x-ray tube of FIG. 9). In a standard x-ray tube, electrons can be emitted at the cathode by heating, and then accelerated by a high voltage potential difference (e.g. 120 kV) towards the anode where they can generate x-rays on impact. In order to pulse an exemplary x-ray tube, the flow of electrons must be interrupted, as opposed to interrupting the flow of x-rays following x-ray generation. Various means of pulsing X-ray tubes may be devised, and the undersampled patterns thereby generated can be used for compressed sensing reconstruction, radiation dose reduction, etc.

Exemplary Realistic Undersampling Model

The exemplary data undersampling model used to generate preliminary data in FIGS. 2A-4 assumes full interruption of the X-ray beam in the non-selected detector-rows, whereas partial blockage can be possible at certain angles and collimator positions. The exemplary system, method, and computer-accessible medium, according to an exemplary embodiment of the present disclosure, can also incorporate no effects of the collimator holes on beam profile, such as penumbral effects or focal spot blurring.

Exemplary Sparse Reconstruction Procedures

Various exemplary sparse reconstruction procedures can be used for robust operation with the realistic undersampling model. For example, beam profile effects can be included in the acquisition matrix A, which can be used in the iterations to improve data consistency. By including the expected profile of partially attenuated projections and differential blurring as a function of time/gantry-angle/collimator-motion explicitly in forward and adjoint operators, an improvement can be achieved in the sharpness and the accuracy of the exemplary reconstructions. The data consistency term in Eq. (1) can also be modified to a maximum-likelihood estimation ("MLE") framework in consideration of CT noise statistics (e.g., shot-noise, Poisson distribution), and this exemplary approach can be compared to an exemplary least-squares framework.

In order to represent realistic anatomy efficiently, several 3D sparsifying transforms, such as orthogonal wavelets, finite differences (e.g., total variation), and geometrically oriented wavelets such as curvelets (see Ref. 37) and shearlets (See Ref. 38), and various combinations of these transforms, can be evaluated based on the compression ratio they can achieve (e.g., as evaluated first in fully-sampled images) and on computational burden. The resulting sparse reconstruction procedures and sparsifying transforms can be implemented using parallel computing techniques on graphical processor units ("GPU") for fast reconstruction. The major limitation on reconstruction speed can be the evaluation of the forward and backward acquisition operator A in each iteration. Prior work has shown that GPUs can be particularly efficient for these types of operations (see Refs. 39 and 40). Besides parallel implementation of the reconstruction procedures, convex optimization procedures can be used with faster convergence, such as, fast iterative soft thresholding ("FISTA") (See Ref. 41), primal-dual approaches, and various other approaches.

For reconstruction performance evaluation, the undersampling model can be applied to fully-sampled acquisitions performed on the American College of Radiology ("ACR") CT accreditation phantom (e.g., Gammex 464) (See Ref. 42). The ACR phantom can be composed of 4 separate sections to individually evaluate slice width, low-contrast resolution, noise and uniformity, and high-contrast resolution. Specifically, the image quality assessment can focus on detectability of low-contrast and high-resolution features, which can be most affected by the usual artifacts in compressed sensing reconstructions at high undersampling factors. Quantitative image quality assessment can be performed using fully-sampled images as ground-truth to compute root mean square error ("RMSE") and structural similarity index ("SSIM") (See Ref. 43 ). Additionally, qualitative impressions of the detectability of low-contrast and high-resolution image features with respect to the fully-sampled images can be catalogued.

Figure 10:
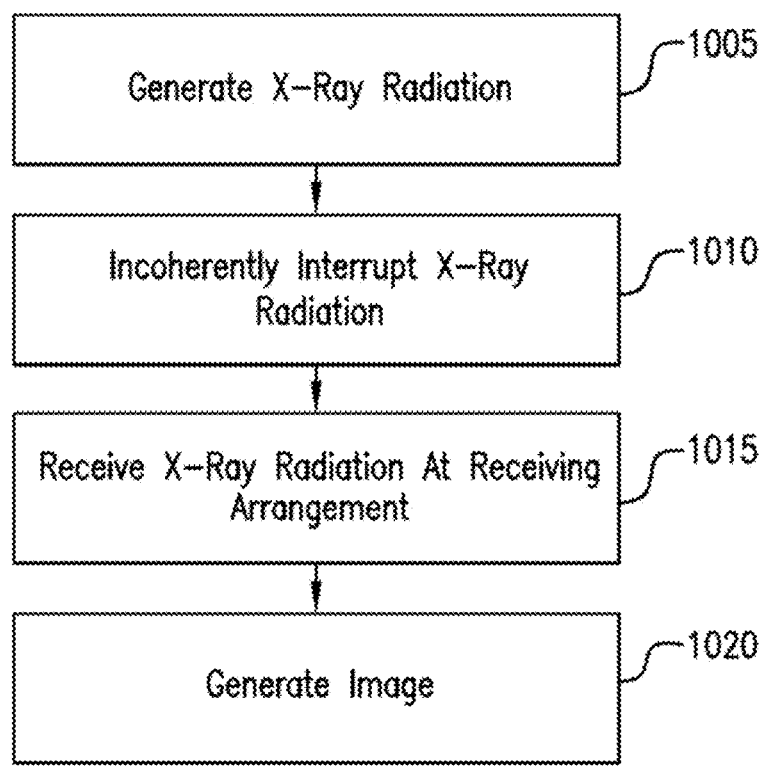
FIG. 10 is an flow diagram illustrating a method for generating an image of an anatomical structure according to an exemplary embodiment of the present disclosure.

FIG. 10 is an exemplary method for generating an image of an anatomical structure. At procedure 1005, x-ray radiation can be generated. At procedure 1010, the x-ray radiation can be incoherently interrupted. At procedure 1015, the incoherently interrupted x-ray radiation is received at an x-ray receiving arrangement. At procedure 1020, the image can be generated, for example, using a compressed sensing procedure.

Exemplary Statistical Methods

In order to test the exemplary system, method and computer-accessible medium, according to an exemplary embodiment of the present disclosure, three sets of imaging data can be evaluated for each patient: (i) the original clinical scan data; (ii) undersampled data, and (iii) reduced-tube-current data, with the latter two sets being derived from the original data using an exemplary simulation tool. Data provided by each of three independent readers can consist of a 5-point ordinal assessment of image quality for each image set, and for the abdominal and chest images, a subject-level binary indicator of whether each reader correctly identified and localized Crohn's disease or pulmonary emboli when using undersampled or reduced-current data relative to consensus reader opinion based on the original data as reference standard.

The three patient groups, corresponding to those providing images of the head, chest or abdomen/pelvis, will be analyzed separately in order to test whether the undersampled images are adequate in each context. An exact Mann-Whitney test can be used to compare image sets in terms of the image quality scores from each reader and in terms of the quality scores represented for each subject as an average over readers. Logistic regression for correlated data can be used to characterize and compare the undersampled and reduced-current image sets in terms of diagnostic accuracy relative to the reference standard. Specifically, generalized estimating equations based on binary logistic regression can be used to model the indicator of a correct diagnosis of the absence or the presence and location of Crohn's disease or pulmonary emboli as a function of image set, reader and institution. The lack of independence among results from the same patient can be accounted for by assuming results from the same patient to be symmetrically correlated and results from different patients to be independent. The output can include a 95% confidence interval ("CI") for the diagnostic accuracy achievable using undersampled or reduced-current data and for the difference between these image sets in terms of diagnostic accuracy. The undersampled data can be deemed non-inferior relative to the full data if the results provide about a 95% confidence that the true mean image quality score of the undersampled images is no more than a half-point lower than the mean score for the original data and if the lower limit of the 95% CI for the diagnostic accuracy associated with the undersampled data relative to the full data is no less than 90%.

Exemplary Statistical Power and Sample Size:

The sample size can be determined such that the exemplary study can have adequate power to assess the non-inferiority of the undersampled data relative to the full data in terms of image quality and diagnostic accuracy. A non-inferiority test of whether the diagnostic accuracy of the undersampled data relative to the full data is at least 90% can benefit from at least about 179 patients in order to achieve about 80% power when the true accuracy is at least 95%. Therefore, data from 200 patients in each of the head, abdomen/pelvis and chest imaging cohorts can be evaluated.

With data from 200 patients, there can be a 95% power to detect a 0.5 point difference between the undersampled and full data sets in terms of true mean image quality score even under the conservative assumption that the within-subject difference between the quality scores of the undersampled and full data sets has a standard deviation as high 2 points.

Figure 11:
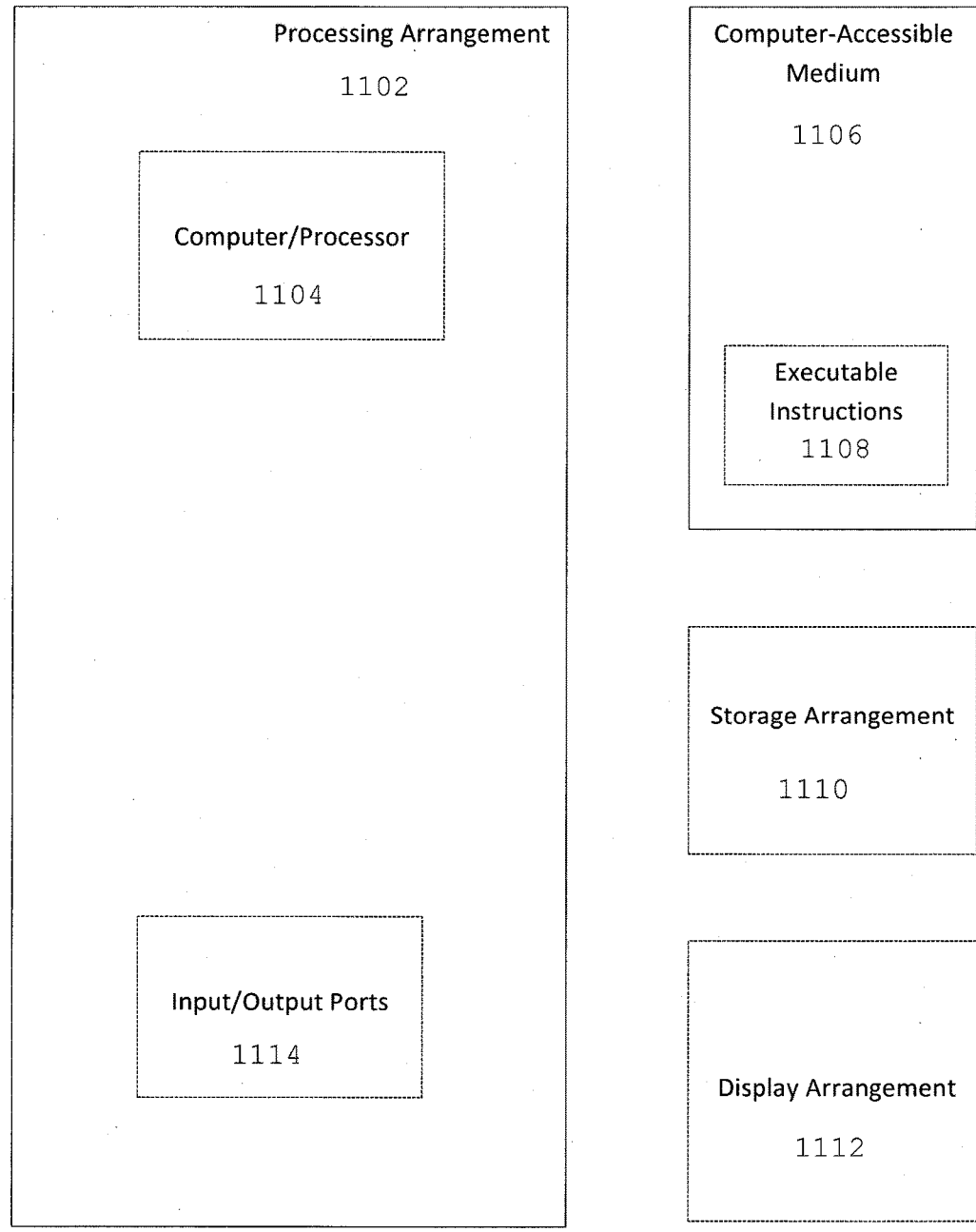
FIG. 11 is an illustration of an exemplary block diagram of an exemplary system in accordance with certain exemplary embodiments of the present disclosure.

FIG. 11 shows a block diagram of an exemplary embodiment of a system according to the present disclosure. For example, exemplary procedures in accordance with the present disclosure described herein can be performed by a processing arrangement and/or a computing arrangement 1102. Such processing/computing arrangement 1102 can be, for example entirely or a part of, or include, but not limited to, a computer/processor 1104 that can include, for example one or more microprocessors, and use instructions stored on a computer-accessible medium (e.g., RAM, ROM, hard drive, or other storage device).

As shown in FIG. 11, for example a computer-accessible medium 1106 (e.g., as described herein above, a storage device such as a hard disk, floppy disk, memory stick, CD-ROM, RAM, ROM, etc., or a collection thereof) can be provided (e.g., in communication with the processing arrangement 1102). The computer-accessible medium 1106 can contain executable instructions 1108 thereon. In addition or alternatively, a storage arrangement 1110 can be provided separately from the computer-accessible medium 1106, which can provide the instructions to the processing arrangement 1102 so as to configure the processing arrangement to 1102 to execute certain exemplary procedures, processes, and methods, as described herein above, for example.

Further, the exemplary processing arrangement 1102 can be provided with or include an input/output ports 1114, which can include, for example a wired network, a wireless network, the internet, an intranet, a data collection probe, a sensor, etc. As shown in FIG. 11, the exemplary processing arrangement 1102 can be in communication with an exemplary display arrangement 1112, which, according to certain exemplary embodiments of the present disclosure, can be a touch-screen configured for inputting information to the processing arrangement in addition to outputting information from the processing arrangement, for example. Further, the exemplary display arrangement 1112 and/or a storage arrangement 1110 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, e.g., data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entirety.
1. Benchmark report CT. Des Plaines: IMV Medical Information Division; 2007.
2. Brenner D J, Hall E J. Computed tomography—an increasing source of radiation exposure. N Engl J Med. 2007; 357(22):2277-84.
3. Sodickson A, Baeyens P F, Andriole K P, Prevedello L M, Nawfel R D, Hanson R, Khorasani R. Recurrent CT, cumulative radiation exposure, and associated radiation-induced cancer risks from CT of adults. Radiology. 2009; 251(1): 175-84.
4. Berrington de Gonzalez A, Mahesh M, Kim K P, Bhargavan M, Lewis R, Mettler F, Land C. Projected cancer risks from computed tomographic scans performed in the United States in 2007. Arch Intern Med. 2009; 169(22): 2071-7.
5. Mettler FAJ, Bhargavan M, Faulkner K, Gilley D B, Gray J E, Ibbott G S, Lipoti J A, Mahesh M, McCrohan J L, Stabin M G, Thomadsen B R, Yoshizumi T T. Radiologic and nuclear medicine studies in the United States and worldwide: frequency, radiation dose, and comparison with other radiation sources-1950-2007. Radiology. 2009; 253(2):520-31.
6. Fazel R, Krumholz H M, Wang Y, Ross J S, Chen J, Ting H H. Exposure to low-dose ionizing radiation from medical imaging procedures. N Engl J Med. 2009; 361(9):849-57.
7. Amis ESJr, Butler P F, Applegate K E, Birnbaum S B, Brateman L F, Hevezi J M, Mettler F A, Morin R L, Pentecost M J, Smith G G, Strauss K J, Zeman R K. American College of Radiology white paper on radiation dose in medicine. J Am Coll Radiol. 2007; 4(5):272-84.
8. Sodickson A. Strategies for reducing radiation exposure in multi-detector row CT. Radiol Clin North Am. 2012; 50(1):1-14.
9. http://www.healthcare.siemens.com/siemens_hwem-hwem_ssxa_websites-context-root/wcm/idc/siemens_h-wem-hwem_ssxa_websites-context-root/wcm/idc/groups/public/@global/@imaging/documents/download/mdax/nju4/~edisp/guide-to-low-dose-2013-00849104.pdf.
10. Kalendar W A. Computed Tomography. 3rd ed. Erlangen, Germany: Publicis Publishing; 2011.
11. McCollough C H, Bruesewitz M R, Kofler J M. CT dose reduction and dose management tools: Overview of available options. Radiographics. 2006; 26(2):503-12.
12. Deak P D, Langner O, Lell M, Kalender W A. Effects of adaptive section collimation on
patient radiation dose in multisection spiral CT. Radiology. 2009; 252(1): 140-7.
13. Shepp L A, Vardi Y. Maximum likelihood reconstruction for emission tomography. IEEE Trans Med Imag. 1982; 1(2):113-22.
14. Grant K, Flohr T. Iterative Reconstruction in Image Space (IRIS). Siemens Healthcare White Paper; A9115-101492. 2010.
15. Grant K, Raupach R. SAFIRE: Sinogram Affirmed Iterative Reconstruction. Siemens Healthcare White Paper. 2011.

16. Hara A K, Paden R G, Silva A C, Kujak J L, Lawder H J, Pavlicek W. Iterative reconstruction technique for reducing body radiation dose at CT: feasibility study. AJR Am J Roentgenol. 2009; 193(3):764-71.
17. Sodickson A, Weiss M. Effects of patient size on radiation dose reduction and image quality in low-kVp CT pulmonary angiography performed with reduced IV contrast dose. Emerg Radiol. 2012; 19(5):437-45.
18. McCollough C H, Chen G H, Kalender W, Leng S, Samei E, Taguchi K, Wang G, Yu L, Pettigrew R I. Achieving routine submillisievert CT scanning: report from the summit on management of radiation dose in CT. Radiology. 2012; 264(2):567-80.
19. Candès E, Romberg J, Tao T. Robust uncertainty principles: Exact signal reconstruction from highly incomplete frequency information. IEEE Trans Inf Theory. 2006.52:489-509.
20. Donoho D. Compressed sensing. IEEE Trans Inf Theory. 2006.52:1289-306.
21. Chen G H, Tang J, Leng S. Prior image constrained compressed sensing (PICCS): a method to accurately reconstruct dynamic CT images from highly undersampled projection data sets. Med Phys. 2008; 35(2):660-3.
22. Brown K, Koehler T, Bergner F, Bippus R, Brendel B, Karl W, Singh S, Padole A, Do S. Sparse sampling for CT dose reduction2013: The 12th International Meeting on Fully Three-Dimensional Image Reconstruction in Radiology and Nuclear Medicine. p. 428-31.
23. Otazo R, Kim D, Axel L, Sodickson D K. Combination of compressed sensing and parallel imaging for highly accelerated first-pass cardiac perfusion MRI. Magn Reson Med. 2010; 64(3):767-76. PubMed Central PMCID: PMC2932824.
24. Feng L, Otazo R, Jung H, Jensen J H, Ye J C, Sodickson D K, Kim D. Accelerated cardiac T2 mapping using breath-hold multiecho fast spin-echo pulse sequence with k-t FOCUSS. Magn Reson Med. 2011; 65(6): 1661-9. PubMed Central PMCID: PMC3097270.
25. Kim D, Dyvorne H A, Otazo R, Feng L, Sodickson D K, Lee V S. Accelerated phase-contrast cine MRI using k-t SPARSE-SENSE. Magn Reson Med. 2012; 67(4): 1054-64. PubMed Central PMCID: PMC3306497.
26. Feng L, Srichai M, Lim P L, Harrison A, King W, Adluru G, Dibella E V, Sodickson D K, Otazo R, Kim D. Highly accelerated real-time cardiac cine MRI using k-t SPARSE-SENSE. Magn Reson Med. 2012; 70(1):64-74.
27. Knoll F, Clason C, Bredies K, Uecker M, Stollberger R. Parallel imaging with nonlinear reconstruction using variational penalties. Magn Reson Med. 2012; 67(1):34-41.
28. Chandarana H, Feng L, Block T K, Rosenkrantz A B, Lim R P, Babb J S, Sodickson D K, Otazo R. Free-breathing contrast-enhanced multiphase MRI of the liver using a combination of compressed sensing, parallel imaging, and golden-angle radial sampling. Invest Radiol. 2013; 48(1):10-6.
29. Feldkamp L A, Davis L C, Kress J W. Practical cone-beam algorithm. J Opt Soc Amer. 1984; A1(6):612-9.
30. Koesters T, Schaefers K P, Wuebbeling F. EMRECON: An expectation maximization based image reconstruction framework for emission tomography data 2011: IEEE Nuclear Science Symposium. p. 4365-68.
31. Loftus E V, Jr., Schoenfeld P, Sandborn W J. The epidemiology and natural history of Crohn's disease in population-based patient cohorts from North America: a systematic review. Aliment Pharmacol Ther. 2002; 16(1): 51-60.
32. Wu Y W, Tang Y H, Hao N X, Tang C Y, Miao F. Crohn's disease: CT enterography manifestations before and after treatment. Eur J Radiol. 2012; 81(1):52-9.
33. Paulsen S R, Huprich J E, Hara A K. CT enterography: noninvasive evaluation of Crohn's disease and obscure gastrointestinal bleed. Radiol Clin North Am. 2007; 45(2):303-15.
34. Hara A K, Swartz P G. CT enterography of Crohn's disease. Abdom Imaging. 2009; 34(3):289-95.
35. Huprich J E, Fletcher J G. CT enterography: principles, technique and utility in Crohn's disease. Eur J Radiol. 2009; 69(3):393-7.
36. Herrinton L J, Liu L, Lewis J D, Griffin P M, Allison J. Incidence and prevalence of inflammatory bowel disease in a Northern California managed care organization, 1996-2002. Am J Gastroenterol. 2008; 103(8):1998-2006.
37. Candes E, Demanet L, Donoho D, Ying L X. Fast discrete curvelet transforms. Multiscle Model Sim. 2006; 5(3):861-99.
38. Guo K, Labate D. Optimally sparse multidimensional representation using shearlets. SIAM J Math Anal. 2007.39:298-318.
39. Knoll F, Unger M, Diwoky C, Clason C, Pock T, Stollberger R. Fast reduction of undersampling artifacts in radial M R angiography with 3D total variation on graphics hardware. MAGMA. 2010; 23(2): 103-14.
40. Freiberger M, Knoll F, Bredies K, Scharfetter H, Stollberger R. The AGILE library for image reconstruction in biomedical sciences using graphics card hardware acceleration. Computing in Science and Engineering 2013.15: 34-44.
41. Beck A, Teboulle M. Fast gradient-based algorithms for constrained total variation image denoising and deblurring problems. IEEE Trans Image Process. 2009; 18(11): 2419-34.
42. McCollough C H, Bruesewitz M R, McNitt-Gray M F, Bush K, Ruckdeschel T, Payne J T, Brink J A, Zeman R K. The phantom portion of the American College of Radiology (ACR) computed tomography (CT) accreditation program: practical tips, artifact examples, and pitfalls to avoid. Med Phys. 2004; 31(9):2423-42.
43. Wang Z, Bovik A C, Sheikh H R, Simoncelli E P. Image quality assessment: From error visibility to structural similarity. IEEE Trans Image Proc. 2004; 13(4):600-12.

What is claimed is:

1. A method for generating at least one image of at least one portion of an anatomical structure, comprising:
    providing a multi-slice computed tomography (CT) scanner that comprises an x-ray source arrangement and a radiation receiving arrangement;
    incoherently interrupting an x-ray radiation beam provided by the x-ray source arrangement that is directed at the at least one portion to generate a resultant x-ray radiation beam having a particular undersampled pattern;
    receiving, at the radiation receiving arrangement, the resultant x-ray radiation beam provided from the at least one portion; and
    generating the at least one image of the at least one portion based on the resultant x-ray radiation beam received at the radiation receiving arrangement.

2. The method of claim 1, further comprising generating the resultant x-ray radiation beam using a multi-hole collimator arrangement.

3. The method of claim 2, wherein the generating of the resultant x-ray radiation beam using a multi-hole collimator arrangement comprises moving the multi-hole collimator arrangement across a path of the x-ray radiation beam.

4. The method of claim 3, wherein the moving of the multi-hole collimator arrangement across the path of the x-ray radiation beam comprises moving the multi-hole collimator arrangement using at least one of a piezoelectric drive, a stepper motor, or a pneumatic drive.

5. The method of claim 1, further comprising generating the resultant x-ray radiation beam using at least one pulsed x-ray tube.

6. The method of claim 1, wherein the multi-slice CT scanner comprises a gantry bore and a gantry table located in the gantry bore, wherein the x-ray source arrangement is located on the gantry bore.

7. The method of clam 6, wherein the particular undersampled pattern is different at adjacent angles of the gantry bore.

8. The method of claim 1, wherein the generating of the at least one image of the at least one portion based on the resultant x-ray radiation beam received at the radiation receiving arrangement comprises generating the at least one image using a compressed sensing reconstruction procedure.

9. The method of claim 8, wherein the compressed sensing reconstruction procedure includes a sparsifying transform including at least one of wavelets, finite differences, or curvelets.

10. An imaging system, comprising:
a multi-slice computed tomography (CT) scanner including an x-ray source first arrangement which provides an x-ray radiation beam; and
a collimating second arrangement configured to incoherently interrupt the x-ray radiation beam provided by the x-ray source first arrangement to generate a resultant x-ray radiation beam having a particular undersampled pattern, which is forwarded to at least one portion of an anatomical structure; and
a third hardware arrangement configured to receive a further x-ray radiation beam from the at least one portion that is based on the resultant x-ray radiation beam, wherein the third hardware arrangement is included in the multi-slice CT scanner.

11. The system of claim 10, wherein the collimating second arrangement comprises a multi-hole collimator arrangement.

12. The system of claim 11, wherein the multi-hole collimator arrangement is configured to move across a path of the x-ray radiation beam.

13. The system of claim 12, further comprising at least one of a piezoelectric drive, a stepper motor, or a pneumatic drive, which is configured to move the multi-hole collimator arrangement.

14. The system of claim 11, wherein the multi-hole collimator arrangement is configured to reduce a number of x-ray radiations along a detector array fan angle or cone angle between the x-ray source first arrangement and the third hardware arrangement.

15. The system of claim 10, wherein the x-ray source first arrangement comprises at least one pulsed x-ray tube.

16. The system of claim 10, wherein the multi sliced CT scanner further comprises a gantry bore and a gantry table located in the gantry bore, wherein the x-ray source first arrangement is located on the gantry bore.

17. The system of claim 16, wherein the particular undersampled pattern is different at adjacent angles of the gantry bore.

18. The system of claim 10, wherein the third arrangement includes a fourth hardware arrangement which is configured to generate at least one image of the at least one portion using compressed sensing reconstruction procedure as a function of the further x-ray radiation beam.

19. The system of claim 18, wherein the compressed sensing reconstruction procedure includes a sparsifying transform including at least one of wavelets, finite differences, or curvelets.

* * * * *